United States Patent [19]

Kuwada et al.

[11] 4,175,079
[45] Nov. 20, 1979

[54] BENZODIAZEPINE DERIVATIVES

[75] Inventors: Yutaka Kuwada, Ashiya; Hideaki Natsugari, Itami; Kanji Meguro, Takarazuka, all of Japan

[73] Assignee: Takeda Chemical Industries, Ltd., Osaka, Japan

[21] Appl. No.: 295,575

[22] Filed: Oct. 6, 1972

[30] Foreign Application Priority Data

Oct. 21, 1971 [JP] Japan .................. 46-83476

[51] Int. Cl.$^2$ .................. A61K 31/55; C07D 487/04
[52] U.S. Cl. .................. 260/243.3; 424/251; 424/244; 260/239 BD
[58] Field of Search .................. 260/239.3 BD, 243.3, 260/256.4 F; 544/250

[56] References Cited

U.S. PATENT DOCUMENTS 3,734,912  5/1973  Hanze ..................... 260/256.4 F Primary Examiner—Alton D. Rollins
Assistant Examiner—James H. Turnipseed
Attorney, Agent, or Firm—Wenderoth, Lind & Ponack

[57] ABSTRACT

The present invention relates to pyrimidobenzodiazepine derivatives of the formula (I) and 2-(N-acetoacetal-)aminobenzodiazepine derivatives of the formula (II), which compounds have the following formulas:

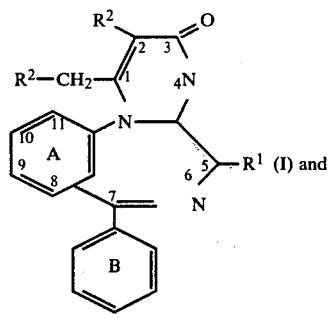

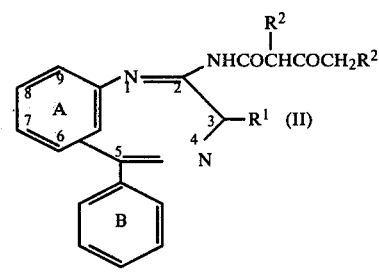

wherein $R^1$ represents a hydrogen atom or a lower alkyl group, $R^2$ represents a hydrogen atom, a lower alkyl group or an aryl group, and rings A and/or B are unsubstituted or substituted by one or more of a halogen, nitro, trifluoromethyl, lower alkyl or lower alkoxy group; including the cases wherein the nitrogen atom at the 6-position of the compound (I) or the 4-position of the compound (II) may be in the form of N-oxide and wherein compound (I) may be in the form of a pharmaceutically acceptable acid addition salt thereof. The present invention also relates to a method of producing these compounds. The compounds (I) and (II) are useful as muscle relaxants, anticonvulsants, sedatives, tranquilizers, etc.

3 Claims, No Drawings

BENZODIAZEPINE DERIVATIVES

This invention relates to novel and useful benzodiazepine derivatives. More particularly, the present invention relates to pyrimidobenzodiazepine derivatives of the formula (I) and 2-(N-acetoacetyl)aminobenzodiazepine derivatives of the formula (II);

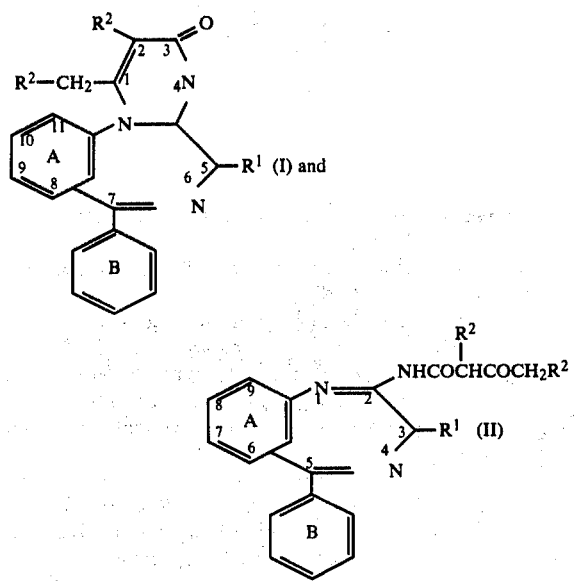

wherein $R^1$ represents hydrogen atom or a lower alkyl group, $R^2$ represents hydrogen atom, a lower alkyl group or an aryl group, and rings A and/or B are unsubstituted or substituted by one or more of halogen, nitro, trifluoromethyl, lower alkyl or lower alkoxy; including the case where nitrogen atom at the 6-position of the compound (I) or the 4-position of the compound (II) may be in a form of N-oxide and to pharmaceutically acceptable acid addition salts of the compound (I), and, further, to the production of these compounds.

The novel compounds (I) and (II) are useful as muscle relaxants, anticonvulsants, sedatives, tranquillizers, etc.

Referring to the formulae (I) and (II), as the lower alkyl group represented by $R^1$ and $R^2$, there are generally mentioned those having 1 to 3 carbon atoms, which include for example methyl, ethyl, propyl or isopropyl. The aryl group represented by $R^2$ is exemplified by phenyl or tolyl.

Rings A and/or B are unsubstituted or substituted in their optional position(s) by one or more substituents, which can be the same with or different from each other, selected from halogen atom (i.e. fluorine, chlorine, iodine and bromine), nitro, trifluoromethyl, a lower alkyl (e.g. methyl, ethyl, propyl, isopropyl) or a lower alkoxy group (e.g. methoxy, ethoxy, propoxy, isopropoxy).

The compounds (I) can be produced by subjecting a compound (II) to a ring-closure reaction in the presence of a dehydrating agent; and, when the product is in a form of N-oxide at the 6-position, the product may be subjected to deoxygenation, and when the product is not in a form of N-oxide at the 6-position, the product may be subjected to oxidation.

The compounds (II) can be produced by reacting the compound of the formula

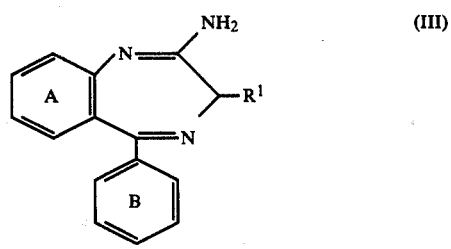

wherein $R^1$, rings A and/or B have the same meanings as defined above; including the case where nitrogen atom at the 4-position may be in a form of N-oxide with a diketene derivative of the formula

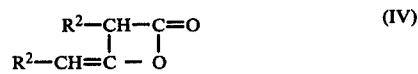

wherein $R^2$ has the same meaning as defined above.

The reactions of the production of the compounds (I) and (II) are shown in the following schema:

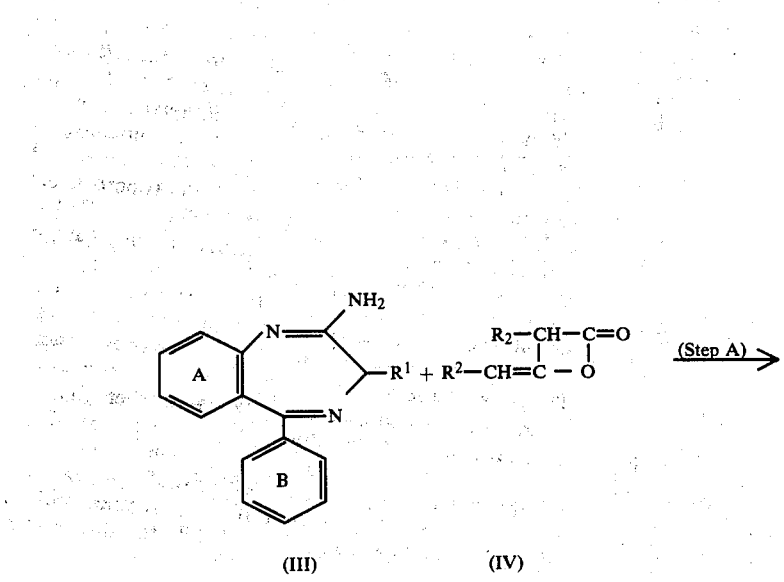

-continued

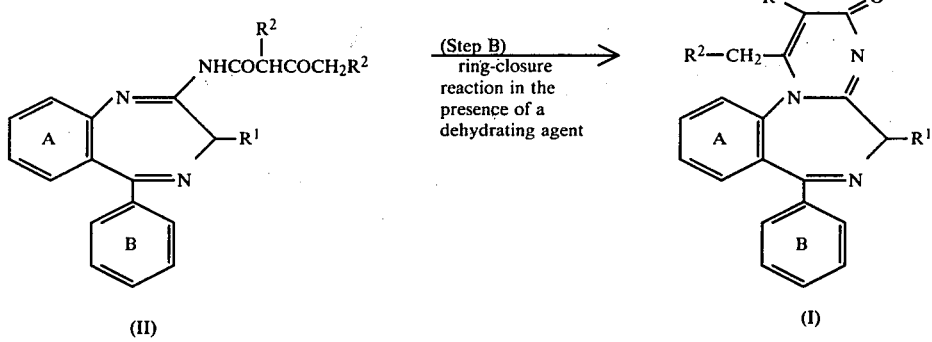

The reaction of Step [A] is conducted by reacting a compound (III) with a diketene derivative (IV). The amount of diketene derivative (IV) is generally 1 to 20 moles, more preferably 1 to 5 moles per mole of the compound (III). This reaction may be conducted in the presence or the absence of a solvent. The solvent may for example be an inert one, such as aromatic hydrocarbons (e.g. benzene, toluene, xylene), aliphatic halogenated hydrocarbons (e.g. chloroform, carbon tetrachloride, methylene chloride), ethers (e.g. tetrahydrofuran, dioxane, ethyl ether) and esters (e.g. ethyl acetate). Instead, the compound (IV) may be employed in a large excess, so that it will act both as a reactant and as a solvent. The reaction is conducted at $-20°$ C. to 80° C., more preferably at room temperature, i.e. 15° C. to 25° C., and, if necessary, it may be conducted at a temperature higher or lower than the above-mentioned range.

In this reaction Step [A], a diketene derivative (IV) reacts with the 2-amino group of the compound (III) to yield the 2-(N-acetoacetyl)aminobenzodiazepine derivative (II). After completion of the reaction, the compound (II) is not necessarily purified, and the residue obtained by the removal of the solvent may be employed to the subsequent reaction. If desired, the compound (II) may be isolated and purified by per se conventional methods and, then, subjected to the next Step [B].

The reaction Step [B] is conducted by subjecting the compound (II) obtained in Step [A] to a ring-closure reaction in the presence of a dehydrating agent, and, when the product is in a form of N-oxide at the 6-position, the product may be subjected to deoxygenation, and when the product is not in a form of N-oxide at the 6-position, the product may be subjected to oxidation.

As the dehydrating agents, they may be exemplified by an acid such as inorganic acid (e.g. hydrogen chloride, hydrogen bromide, sulfuric acid, phosphoric acid, polyphosphoric acid), organic carboxylic acid (e.g. acetic acid, propionic acid, trifluoroacetic acid), organic sulfonic acid (e.g. methanesulfonic acid, benzenesulfonic acid, toluenesulfonic acid), or a chloride such as thionylchloride, phosphorus oxychloride. The amount of the dehydrating agent is generally 1 to 20 moles, more preferably 2 to 10 moles per mole of the compound (II).

The reaction may be conducted in the presence or the absence of a solvent. The solvent is exemplified by alcohols (e.g. methanol, ethanol, propanol), aliphatic halogenated hydrocarbons (e.g. chloroform, methylene chloride), aromatic hydrocarbons (e.g. benzene, toluene, xylene), ethers (e.g. tetrahydrofuran, dioxane, ethyl ether) and esters (e.g. ethyl acetate).

The reaction is conducted at $-20°$ C. to 120° C., more preferably $-10°$ C. to 50° C.

When an acid is used as a dehydrating agent in Step [B], the compound (I) is obtained as the acid addition salt. The acid adduct may easily be converted to its free base by per se conventional means, for example using ammonia, alkali hydroxide, alkali carbonate or alkali bicarbonate.

In case where the compound (I) is in a form of a free base, if desired, it may be converted to the corresponding acid addition salt by treating it with a suitable acid after per se conventional means. As the acids, they may be, for example, an inorganic acid (e.g. hydrochloric acid, hydrobromic acid, sulfuric acid, phosphoric acid).

When nitrogen atom at the 6-position of the compound (I) carries oxygen atom, N-oxide can be, if necessary, deoxygenated to the corresponding compound (I) wherein nitrogen atom at the 6-position carries no oxygen atom. The deoxygenation can be conducted by conventional means, for example, treating the compound with a suitable deoxygenating agent (e.g. phosphorus trichloride; trisubstituted phosphite such as trimethyl phosphite, triethyl phosphite; or trisubstituted phosphines such as triethyl phosphine, triphenyl phosphine) at 0° C. to 150° C. in a suitable inert solvent such as hydrocarbons or halogenated hydrocarbons, or catalytic reduction using Raney nickel at 0° C. to 100° C. in a suitable inert solvent such as alcohols, hydrocarbons, halogenated hydrocarbons.

Moreover, when nitrogen atom at the 6-position of compound (I) carries no oxygen atom, the nitrogen atom can be, if necessary, oxidized to N-oxide. The oxidation, can be conducted by conventional means, for example, by treating the compound with a suitable oxidizing agent (e.g. perbenzoic acid, ortho-, meta- and para-chloroperbenzoic acid, 3,5-dichloroperbenzoic acid, 4-methylperbenzoic acid), at $-20°$ C. to 200° C. in a suitable inert solvent such as hydrocarbons, halogenated hydrocarbons, and alcohols.

The compound (I), its acid addition salt and the compound (II), all of which are novel compounds, are pharmacologically active on the central nervous system. They are of use as muscle-relaxants, anti-convulsants, tranquillizers, sedatives, hypnotics and other pharmaceuticals, and can be administered as such or, if required, in admixture with an inert vehicle which is pharmacologically acceptable, either orally or parenterally in various forms such as powders, granules, tablets, capsules, liquids and injections. While the dose varies with kinds of compounds, symptoms and other factors, it generally ranges from about 1 to about 30 mg. for human adults per day by oral administration.

For further detailed explanation of the invention, the following examples are given, wherein the term "part(s)" means "weight part(s)" unless otherwise noted and the relationship between "part(s)" and "part(s) by volume" corresponds to that between "gram(s)" and "milliliter(s)".

EXAMPLE 1

To a stirred suspension of 0.27 parts of 2-amino-7-chloro-5-phenyl-3H-1,4-benzodiazepine in 5 parts by volume of chloroform is added 0.15 part by volume of diketene at 25° C., and the mixture is stirred for 1.5 hour. To this solution are added 10 parts by volume of chloroform and 20 parts by volume of water and, after vigorous shaking, the chloroform layer is separated, washed with water and dried over sodium sulfate. After removal of the solvent under reduced pressure, the residue is treated with n-hexane-ether, whereupon 2-acetoacetamido-7-chloro-5-phenyl-3H-1,4-benzodiazepine is obtained as crystals. Recrystallization from methylene chloride-n-hexane yields pale yellow powdery crystals, m.p. 148°–148.5° C.

To a suspension of 3 parts of 2-acetoacetamido-7-chloro-5-phenyl-3H-1,4-benzodiazepine in 35 parts by volume of methanol is added dropwise 5 parts by volume of methanol saturated with hydrogen chloride with stirring and cooling with ice-salt. After stirring 1 hour, the mixture is poured into a cooled mixture of 20 parts by volume of concentrated aqueous ammonia and 100 parts by volume of water and then extracted with chloroform. The chloroform layer is washed with water and dried over sodium sulfate. Evaporation of the solvent and then treatment of the residue with n-hexane-ether gives crystals, which are collected by filtration, washed with ether and dried. This procedure yields 9-chloro-3,5-dihydro-1-methyl-7-phenylpyrimido[1,2-a]-[1,4]benzodiazepin-3-one as crystals. Recrystallization from methylene chloride-isopropyl ether gives fine colorless needles melting at 232°–234° C. (decomp.).

EXAMPLE 2

The following compounds are prepared in a similar manner to that in Example 1.

|  |  | Compound (III) | Compound (II) | Compound (I) |
| --- | --- | --- | --- | --- |
| 2 a | 2-amino-7-chloro-5-phenyl-3H-1,4-benzodiazepine 4N-oxide | 2-acetoacetamido-7-chloro-5-phenyl-3H-1,4-benzodiazepine 4N-oxide. m.p. 255°–257° C. (decomp.) | 9-chloro-3,5-dihydro-1-methyl-7-phenyl-pyrimido[1,2-a][1,4]-benzodiazepin-3-one 6N-oxide. m.p. 243°–245° C. (decomp.) |
| 2 b | 2-amino-5-phenyl-7-trifluoro-methyl-3H-1,4-benzodiazepine 4N-oxide | 2-acetoacetamido-5-phenyl-7-trifluoro-methyl-3H-1,4-benzodiazepine 4N-oxide. m.p. 218°–219° C.(decomp.) | 3,5-dihydro-1-methyl-7-phenyl-9-trifluoro-methylpyrimido[1,2-a]-[1,4]benzodiazepin-3-one 6N-oxide. m.p. 250°–251° C. (decomp.) |
| 2 c | 2-amino-7-nitro-5-phenyl-3H-1,4-benzodiazepine 4N-oxide | 2-acetoacetamido-7-nitro-5-phenyl-3H-1,4-benzodiazepine 4N-oxide. m.p. 167°–169° C. (decomp.) | 3,5-dihydro-1-methyl-9-nitro-7-phenyl-pyrimido[1,2-a][1,4]-benzodiazepin-3-one 6N-oxide. m.p. 240°–242° C. (decomp.) |
| 2 d | 2-amino-5-phenyl-3H-1,4-benzodiazepine | 2-acetoacetamido-5-phenyl-3H-1,4-benzodiazepine. oily product | 3,5-dihydro-1-methyl-7-phenylpyrimido-[1,2-a][1,4]benzo-diazepin-3-one. m.p. 192°–193° C. (decomp.) |
| 2 e | 2-amino-7-nitro-5-phenyl-3H-1,4-benzodiazepine | 2-acetoacetamido-7-nitro-5-phenyl-3H-1,4-benzodiazepine. oily product | 3,5-dihydro-1-methyl-9-nitro-7-phenyl-pyrimido[1,2-a][1,4]-benzodiazepin-3-one. m.p. >280° C. |
| 2 f | 2-amino-7-methyl-5-phenyl-3H-1,4-benzodiazepine | 2-acetoacetamido-7-methyl-5-phenyl-3H-1,4-benzodiazepine. oily product | 3,5-dihydro-1,9-dimethyl-7-phenyl-pyrimido[1,2-a][1,4]-benzodiazepin-3-one. m.p. 205°–207° C. (decomp.) |
| 2 g | 2-amino-7-chloro-5-(4-methoxy-phenyl)-3H-1,4-benzodiazepine | 2-acetoacetamido-7-chloro-5-(4-methoxy-phenyl)-3H-1,4-benzodiazepine. oily product | 9-chloro-3,5-dihydro-7-(4-methoxyphenyl)-1-methyl-pyrimido[1,2-a][1,4]-benzodiazepin-3-one. m.p. 249°–250° C. (decomp.) |
| 2 h | 2-amino-7-chloro-5-(2-chloro-phenyl)-3H-1,4-benzodiazepine | 2-acetoacetamido-7-chloro-5-(2-chlorophenyl)-3H-1,4-benzodiazepine. oily product | 9-chloro-7-(2-chlorophenyl)-3,5-dihydro-1-methyl-pyrimido[1,2-a][1,4]-benzodiazepin-3-one. hemihydrate m.p. 169°–171° C. |

EXAMPLE 3

A mixture of 0.5 part of 9-chloro-3,5-dihydro-1-methyl-7-phenylpyrimido[1,2-a][1,4]benzodiazepin-3-one 6N-oxide 30 parts by volume of chloroform and 1 part of phosphorus trichloride is refluxed for 10 minutes. After evaporation of the solvent under reduced pressure, the residue is partitioned between chloroform and an aqueous sodium hydroxide solution. The chloroform layer separated is washed with water and concentrated. The residue is purified by chromatography on silica gel [solvent system: chloroform-methanol-ethyl acetate (85:10:5)], whereupon 9-chloro-3,5-dihydro-1-methyl-7-phenylpyrimido[1,2-a][1,4]benzodiazepin-3-one is obtained as crystals melting at 232°–234° C. (decomp.). This compound is identical with the sample prepared in Example 1.

EXAMPLE 4

To a solution of 1 part of 9-chloro-3,5-dihydro-1-methyl-7-phenylpyrimido[1,2-a][1,4]benzodiazepine in 50 parts by volume of dichloromethane is added 1 part of metachloroperbenzoic acid under stirring at 25° C. The reaction mixture is allowed to stand for 15 hours at 25° C., then treated with sodium bicarbonate solution. Dichloromethane layer is separated, washed with water and then dried over sodium sulfate. After removal of the solvent, the oil residue is purified by means of chromatography on silica gel [solvent system: chloroform-methanol-ethyl acetate (85:10:5)] to give 9-chloro-3,5-dihydro-1-methyl-7-phenylpyrimido[1,2-a][1,4]benzodiazepin-3-one 6N-oxide as colorless crystals melting at 242°–244° C. (decomposition). This compound is identical with the one prepared in Example 2-a.

Some examples of practical recipes in which the compounds of this invention are utilized as remedies for a tranquillizer are as follows:

| Tablet: | |
|---|---|
| | (milligram) |
| (9-chloro-3,5-dihydro-1-methyl-7-phenylpyrimido[1,2-a][1,4]benzodiazepin-3-one | 2 |
| lactose | 60 |
| corn starch | 36.5 |
| gelatin | 1 |
| magnesium stearate | 0.5 |
| | 100 milligrams per tablet |

| Tablet: | |
|---|---|
| | (milligram) |
| 9-chloro-3,5-dihydro-1-methyl-7-phenylpyrimido[1,2-a][1,4]-benzodiazepin-3-one | 10 |
| lactose | 60 |
| corn starch | 28.5 |
| gelatin | 1 |
| magnesium stearate | 0.5 |
| | 100 milligrams per tablet |

What we claim is:

1. The compound 9-chloro-7-(2-chlorophenyl)-3,5-dihydro-1-methylpyrimido[1,2-a][1,4]benzodiazepin-3-one.

2. A method for producing a compound of the formula:

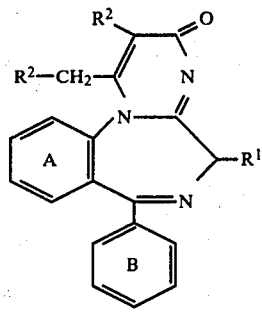

wherein $R^1$ is hydrogen or lower alkyl having 1 to 3 carbon atoms; $R^2$ is hydrogen, lower alkyl having 1 to 3 carbon atoms, phenyl or tolyl, and rings A and/or B are unsubstituted or monosubstituted by halogen, nitro, trifluoromethyl, lower alkyl having 1 to 3 carbon atoms or lower alkoxy having 1 to 3 carbon atoms, and wherein the nitrogen atom at the 6-position may be in the form of N-oxide, or pharmaceutically acceptable acid addition salts of the compounds which method comprises the steps of subjecting a compound of the formula

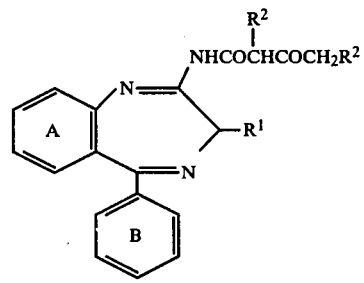

wherein $R^1$, $R^2$ and rings A and/or B have the same meanings as defined above; including the case where the nitrogen atom at the 4-position may be in a form of N-oxide, to a ring-closure reaction in the presence of a dehydrating agent which is an acid selected from the group consisting of hydrogen chloride, hydrogen bromide, sulfuric acid, phosphoric acid, polyphosphoric acid, acetic acid, propionic acid, trifluoroacetic acid, methane sulfonic acid, benzenesulfonic acid, toluenesulfonic acid, thionylchloride and phosphorous oxychloride; and, when the product is in a form of N-oxide at the 6-position, the product may be subjected to deoxygenation by reaction with phosphorous trichloride, and when the product is not in a form of N-oxide at the 6-position, the product may be subjected to oxidation by reaction with metachloroperbenzoic acid.

3. A method for producing a compound of the formula

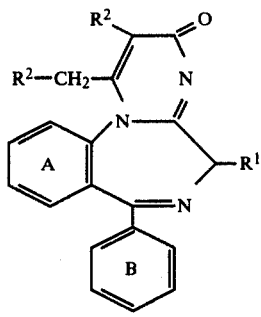

wherein $R^1$ is hydrogen or lower alkyl having 1 to 3 carbon atoms; $R^2$ is hydrogen, lower alkyl having 1 to 3 carbon atoms, phenyl or tolyl, and rings A and/or B are unsubstituted or monosubstituted by halogen, nitro, trifluoromethyl, lower alkyl having 1 to 3 carbon atoms or lower alkoxy having 1 to 3 carbon atoms, and wherein the nitrogen atom at the 6-position may be in the form of N-oxide, or pharmaceutically acceptable acid addition salts of the compounds which method comprises the steps of reacting a compound of the formula

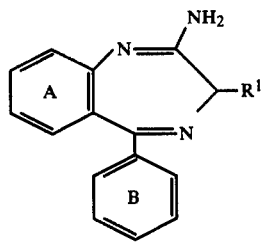

wherein $R^1$ and rings A and/or B have the same meanings as defined above; including the case where the nitrogen atom at the 4-position may be in a form of N-oxide with a diketene derivative of the formula

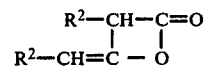

wherein $R^2$ has the same meaning as defined above to give a compound of the formula

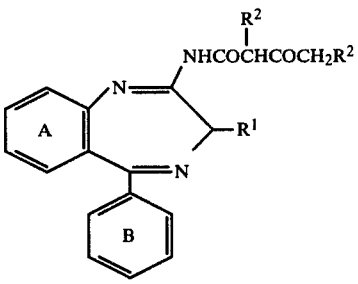

wherein $R^1$, $R^2$ and rings A and/or B have the same meanings as defined above; including the case where the nitrogen atom at the 4-position may be in the form of N-oxide, and then subjecting the compound produced to a ring-closure reaction in the presence of a dehydrating agent which is an acid selected from the group consisting of hydrogen chloride, hydrogen bromide, sulfuric acid, phosphoric acid, polyphosphoric acid, acetic acid, propionic acid, trifluoroacetic acid, methanesulfonic acid, benzenesulfonic acid, toluenesulfonic acid, thionylchloride, and phosphorous oxychloride; and, when the product is in a form of N-oxide at the 6-position, the product may be subjected to deoxygenation by reaction with phosphorous trichloride, and when the product is not in a form of N-oxide at the 6-position, the product may be subjected to oxidation by reaction with metachloroperbenzoic acid.

* * * * *